(12) United States Patent
Riviere et al.

(10) Patent No.: US 8,162,925 B2
(45) Date of Patent: Apr. 24, 2012

(54) ROBOT FOR MINIMALLY INVASIVE INTERVENTIONS

(75) Inventors: Cameron N. Riviere, Pittsburgh, PA (US); Nicholas A. Patronik, Pittsburgh, PA (US); Marco A. Zenati, Pittsburgh, PA (US); George D. Stetten, Pittsburgh, PA (US)

(73) Assignees: Carnegie Mellon University, Pittsburgh, PA (US); University of Pittsburgh of the Commonwealth System of Higher Education, Pittsburgh, PA (US)

( * ) Notice: Subject to any disclaimer, the term of this patent is extended or adjusted under 35 U.S.C. 154(b) by 1177 days.

(21) Appl. No.: 10/982,670

(22) Filed: Nov. 5, 2004

(65) Prior Publication Data

US 2005/0154376 A1 Jul. 14, 2005

Related U.S. Application Data

(60) Provisional application No. 60/518,582, filed on Nov. 7, 2003.

(51) Int. Cl.
*A61B 17/00* (2006.01)
(52) U.S. Cl. .......................................... 606/1
(58) Field of Classification Search ................. 606/123, 606/139; 318/568.12; 74/490
See application file for complete search history.

(56) References Cited

U.S. PATENT DOCUMENTS

| | | |
|---|---|---|
| 1,128,746 A | 2/1915 | Bierce |
| 4,148,307 A | 4/1979 | Utsugi |
| 4,522,129 A | 6/1985 | Jerberyd |
| 4,848,168 A | 7/1989 | Negishi |
| 4,938,081 A | 7/1990 | Negishi |
| 5,018,451 A | 5/1991 | Hapstack |
| 5,077,510 A | 12/1991 | Collie |

(Continued)

FOREIGN PATENT DOCUMENTS

JP 5-43114 6/1993

(Continued)

OTHER PUBLICATIONS

N. Simaana et al., A Dextrous System for Laryngeal Surgery, Proceedings of the 2004 IEEE Int'l. Conference on Robotics & Automation, Apr. 2004, pp. 1-7, New Orleans, LA.

(Continued)

*Primary Examiner* — Ryan Severson
*Assistant Examiner* — Sarah Simpson
(74) *Attorney, Agent, or Firm* — Weingarten, Schurgin, Gagnebin & Lebovici LLP (57) ABSTRACT

Rather than trying to immobilize a living, moving organ to place the organ in the fixed frame of reference of a table-mounted robotic device, the present disclosure teaches mounting a robot in the moving frame of reference of the organ. That task can be accomplished with a wide variety of robots including a miniature crawling robotic device designed to be introduced, in the case of the heart, into the pericardium through a port, attach itself to the epicardial surface, and then, under the direct control of the surgeon, travel to the desired location for treatment. The problem of beating-heart motion is largely avoided by attaching the device directly to the epicardium. The problem of access is resolved by incorporating the capability for locomotion. The device and technique can be used on other organs and on other living bodies such as pets, farm animals, etc. Because of the rules governing abstracts, this abstract should not be used in construing the claims.

28 Claims, 10 Drawing Sheets

U.S. PATENT DOCUMENTS

| | | | |
|---|---|---|---|
| 5,080,020 A | 1/1992 | Negishi | |
| 5,121,694 A | 6/1992 | Zollinger | |
| 5,293,823 A | 3/1994 | Box | |
| 5,382,885 A | 1/1995 | Salcudean et al. | |
| 5,386,741 A | 2/1995 | Rennex | |
| 5,467,813 A | 11/1995 | Vermaat | |
| 5,473,953 A | 12/1995 | Appel | |
| 5,497,707 A | 3/1996 | Box | |
| 5,601,025 A | 2/1997 | Box | |
| 5,662,587 A | 9/1997 | Grundfest et al. | |
| 5,791,255 A | 8/1998 | Box | |
| 5,906,591 A * | 5/1999 | Dario et al. | 604/95.03 |
| 5,906,607 A * | 5/1999 | Taylor et al. | 606/1 |
| 6,240,312 B1 | 5/2001 | Alfano et al. | |
| 6,309,346 B1 | 10/2001 | Farhadi | |
| 6,450,104 B1 | 9/2002 | Grant et al. | |
| 6,484,727 B1 * | 11/2002 | Vaska et al. | 128/898 |
| 6,589,166 B2 * | 7/2003 | Knight et al. | 600/205 |
| 6,633,150 B1 | 10/2003 | Wallach et al. | |
| 6,648,814 B2 | 11/2003 | Kim et al. | |
| 6,699,179 B2 | 3/2004 | Wendlandt | |
| 6,702,734 B2 | 3/2004 | Kim et al. | |
| 6,719,684 B2 | 4/2004 | Kim et al. | |
| 6,764,441 B2 | 7/2004 | Chiel et al. | |
| 6,824,508 B2 | 11/2004 | Kim et al. | |
| 6,936,001 B1 | 8/2005 | Snow | |
| 2002/0107478 A1 | 8/2002 | Wendlandt | |
| 2002/0168317 A1 * | 11/2002 | Daighighian et al. | 424/1.11 |
| 2002/0173700 A1 | 11/2002 | Kim et al. | |
| 2003/0018358 A1 * | 1/2003 | Saadat | 606/232 |
| 2003/0065250 A1 | 4/2003 | Chiel et al. | |
| 2003/0167000 A1 | 9/2003 | Mullick et al. | |
| 2004/0092798 A1 * | 5/2004 | Spence et al. | 600/210 |
| 2005/0119640 A1 * | 6/2005 | Sverduk et al. | 606/1 |

FOREIGN PATENT DOCUMENTS

| | | |
|---|---|---|
| JP | 05-293077 | 11/1993 |
| WO | WO 98/11816 | 3/1998 |
| WO | WO 01/54565 | 8/2001 |
| WO | WO 02/068035 | 9/2002 |

OTHER PUBLICATIONS

C. Menon et al., Gecko Inspired Surface Climbing Robots, IEEE Int'l. Conference on Robotics& Biomimetics, Aug. 2004, pp. 1-6, Shenyang, China.

W. Siegel et al., Mobile Robots for Difficult Measurements in Difficult Environments: Application to Aging Aircraft Inspection, Robotics and Autonomous Systems, 1993, vol. 11, pp. 187-194.

Metin Sitti and Ronald S. Fearing, Synthetic Gecko Foot-Hair Micro/Nano-Structures as Dry Adhesives, Journal of Adhesion Science and Technology, 2003, pp. 1055-1074, vol. 18, No. 7, XP-002319306.

Nicholas A. Patronik, Marco A. Zenati and Cameron N. Riviere, Development of a Tethered Epicardial Crawler for Minimally Invasive Cardiac Therapies, Bioengineering Conference, 2004, Proceedings of the IEEE 30th Annual Northeast Springfield, MA Apr. 17-18, 2004, Piscataway, NJ, USA, IEEE, Apr. 17, 2004, pp. 239-240, XP010706390.

* cited by examiner

ROBOT FOR MINIMALLY INVASIVE INTERVENTIONS

The present application claims priority from U.S. application Ser. No. 60/518,582 filed Nov. 7, 2003 and entitled Inchworm Robot for Minimally Invasive Cardiac Interventions, which is hereby incorporated by reference in its entirety.

BACKGROUND

Heart surgery, particularly the types addressed here (e.g., epicardial electrode placement, atrial ablation) is typically done via either an open approach, or a minimally invasive approach using hand-held rigid endoscopic tools.

Several recent development efforts center around robots intended to perform heart surgery, among other procedures. A commercially available robotic system for cardiac surgery is the da Vinci System available from Intuitive Surgical of Mountain View, Calif. That system is teleoperative, meaning that the motions of the surgeons hands on input devices are mirrored by laparoscopic manipulators located within the body. While such a system can offer superior dexterity to conventional laparoscopic instruments, it requires some form of stabilization for the heart, requires collapsing a lung, has a limited operative field, and is bulky and expensive.

Closed-chest endoscopic visualization of the epicardium was first described by Santos et al. (Ann Thorac Surg 1977; 23: 467-470); subsequent reports have utilized the technique for evaluation of blunt chest trauma, pericardial effusion and lung cancer staging. Lattouf et al have utilized the technique for epicardial implantation of left ventricular pacing leads. In each of these reports, endoscope access required thoracotomy with breach of the left pleural space. Direct access to the pericardial space via subxiphoid puncture is an increasingly practiced technique during catheter ablation procedures. In these reports, once access was achieved, catheter manipulation was guided solely by fluoroscopy. We are aware of cursory attempts at standard pacing lead implantation using this approach which have failed due to inability to achieve fixation.

The challenges of minimally invasive access are further complicated by the goal of avoiding cardiopulmonary bypass, and this goal necessitates surgery on a beating heart. Thus instrumentation is needed that allows stable manipulation of an arbitrary location on the epicardium while the heart is beating. See, for example, published application number 20040172033. Local immobilization of the heart is the approach generally followed with endoscopic stabilizers such as the Endostab device and the endo-Octopus device, which operate with pressure or suction. However, the resulting forces exerted on the myocardium can cause changes in the electrophysiological and hemodynamic performance of the heart, and there has been discussion in the literature regarding the care that must be taken to avoid hemodynamic impairment [Falk, et al., Endoscopic coronary artery bypass grafting on the beating heart using a computer enhanced telemanipulation system. Heart Surg Forum 2: 199-205, 1999]. As an alternative, several researchers in robot-assisted endoscopic surgery are investigating active compensation of heartbeat motion by visually tracking the epicardium and moving the tool tips accordingly [Çavuşoğlu M C, et al., Robotics for telesurgery: second generation Berkeley/UCSF laparoscopic telesurgical workstation and looking towards the future applications. Industrial Robot 30:22-29, 2003; Ortmaier T J. Motion compensation in minimally invasive robotic surgery. Ph.D. dissertation, Technical University of Munich, Germany, 2003.], but this research problem remains open. The motion of the beating heart is complex. In addition to the challenges of modeling or tracking the heart surface, active compensation will require considerable expense for high-bandwidth actuation to enable manipulation in at least three degrees of freedom over a relatively large workspace (See Cavusoglu, supra).

BRIEF SUMMARY

The prior art solutions address a problem that exists only because the tools are held by a surgeon or a robot that is fixed to the table or standing on the floor. The present disclosure takes a different approach. Rather than trying to immobilize the heart surface to stabilize it in the fixed frame of reference of a table-mounted robotic device, we mounted the device in the moving reference frame of the beating heart. That task was accomplished with a miniature crawling robotic device designed to be introduced into the pericardium through a port, attach itself to the epicardial surface, and then, under the direct control of the surgeon, travel to the desired location for treatment. The problem of beating-heart motion was largely avoided by attaching the device directly to the epicardium. The problem of access was resolved by incorporating the capability for locomotion.

Improved access and precise manipulation are not the only benefits of this approach. Port access for minimally invasive cardiac surgery has typically been transthoracic, largely to accommodate the rigid endoscopes generally used for both manual and robot-assisted procedures. Transthoracic access to the heart requires deflation of the left lung, general endotracheal anesthesia, and differential lung ventilation. A variety of current and upcoming procedures, however, can conceivably be performed transpericardially, without invasion of the pleural space, with appropriate instrumentation. Examples include, but are not limited to cell transplantation, gene therapy for angiogenesis, epicardial electrode placement for resynchronization, epicardial atrial ablation, intrapericardial drug delivery, and ventricle-to-coronary artery bypass, among others.

The ability of the device to move to any desired location on the epicardium from any starting point enables minimally invasive cardiac surgery to become independent of the location of the pericardial incision. Use of the device also allows a subxiphoid transpericardial approach to any intrapericardial procedure, regardless of the location of the treatment site. As a result, deflation of the left lung is no longer needed, and it becomes feasible to use local or regional rather than general anesthetic techniques. These advantages have the potential for opening the way to ambulatory outpatient cardiac surgery. The opportunity for "synergy" (e.g. multiple procedures during a single operative session) may prove particularly valuable. The techniques disclosed herein are applicable to other organs within a living body and need not be limited to the human heart, which is merely our first application.

BRIEF DESCRIPTION OF THE DRAWINGS

For the present disclosure to be easily understood and readily practiced, the present disclosure will now be described, for purposes of illustration and not limitation, in connection with the following figures wherein:

FIG. 5A illustrates another embodiment of a robot and control system according to the present disclosure while

FIG. 6A is an example of one type of end effector, a semicircular needle, retracted into a recessed storage location in the distal body while

DETAILED DESCRIPTION

Figure 1:
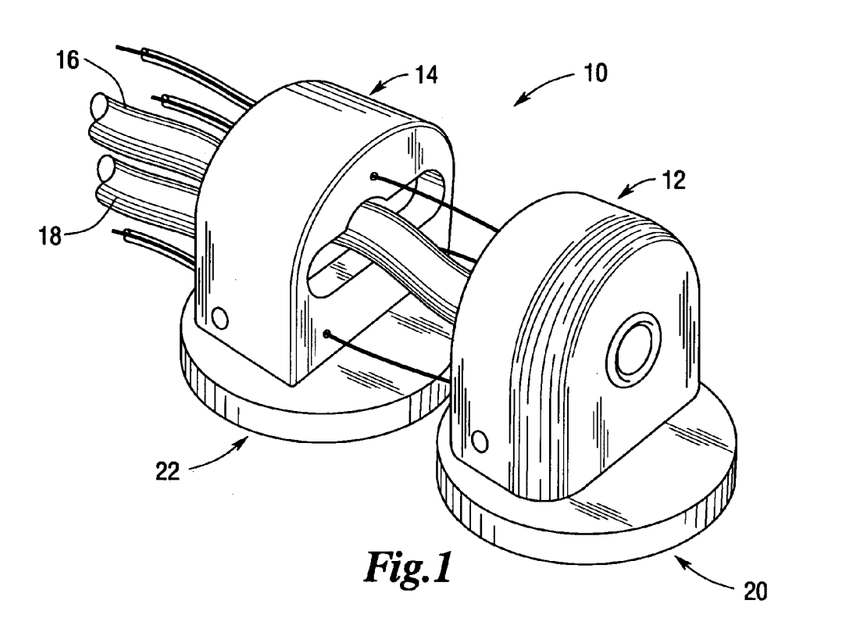
FIG. 1 is a forward isometric view of the distal body and proximal body which, together with the control wires and suction lines, makeup one embodiment of the robot.
Figure 2:
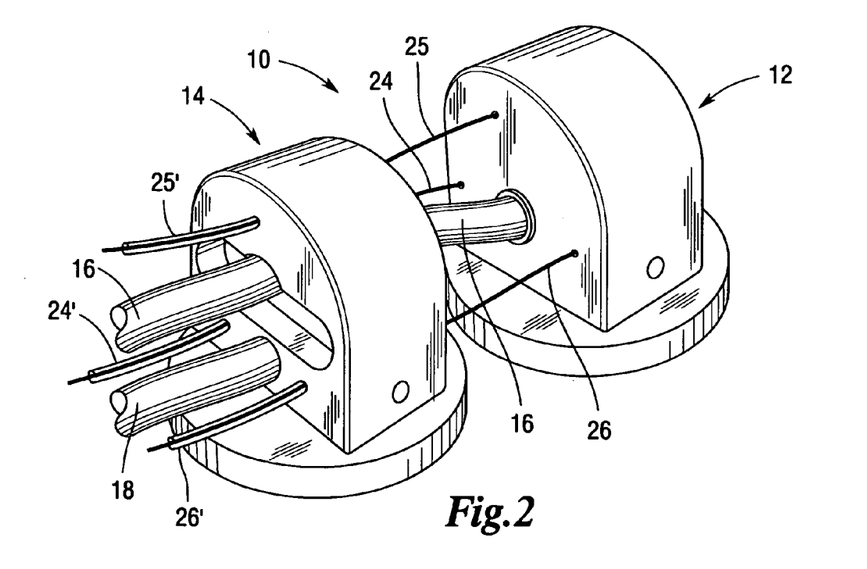
FIG. 2 is a rearward isometric view of the distal and proximal bodies of FIG. 1.

One embodiment of a robot constructed according to the present disclosure is illustrated in FIGS. 1 and 2. FIGS. 1 and 2 illustrate a prototype device 10 designed and constructed in the Medical Instrumentation Lab at Carnegie Mellon University, which will now be described for purposes of illustration and not limitation. The device 10 consists of two glass-filled polycarbonate shells forming a distal body 12 and a proximal body 14, each body having a 13 mm circular footprint and a height of 14 mm. That size allows the device 10 to fit within a standard 20 mm diameter cannula or port. Each of the body sections 12, 14 is equipped with an independent suction line 16, 18 and suction pad 20, 22, respectively, for gripping to biological tissue. The suction lines 16, 18 and suction pads 20, 22 illustrate one type of means for prehension.

The translation and rotation of the body sections 12, 14 relative to one another are controlled from an external control system, in this embodiment a handle 15 (shown in FIGS. 3A-3D and FIGS. 4A-4C), by manually adjusting the lengths of three nitinol wires 24, 25, 26 running along the longitudinal axis of the device 10. The super-elasticity of nitinol allows the wires to support tension and compression (i.e. pulling and pushing) without permanently deforming. That eliminates the need for shape restoring components (like springs) that are required in some other systems. The axes of these wires 24, 25, 26 intersect the body sections 12, 14 at the perimeter of a 10 mm diameter circle at 120-degree intervals. The wires 24, 25, 26 are fixed to the distal body 12 and pass freely through the proximal body 14 out to the handle 15 of the device. Between the proximal body 14 and the handle 15, the wires 24, 25, 26 are contained within sheaths 24', 25', 26', respectively, e.g. flexible plastic tubing, whose ends are attached to the proximal body 14 and the handle 15. The three independently actuated wires 24, 25, 26 provide three degrees of freedom between the distal body 12 and the proximal body 14, two angular and one translational. The two angular degrees of freedom allow the device 10 to adapt to the curvature of the heart (or other organ) as well as turn laterally (i.e. yaw).

The sheaths 24', 25', 26' prevent bowing of the wires 24, 25, 26 so as to transmit the forces applied to the wires 24, 25, 26, respectively, at the handle 15 to either proximal body 14 or distal body 12 and ensure that the length of wires 24, 25, 26 between the handle 15 and proximal body 14 remains constant. Thus, when the length of a wire exiting its sheath at the handle is changed, the length of that wire between the proximal body 14 and the distal body 12 changes by the same amount.

Inchworm-like locomotion is achieved by alternating the suction force exerted by the two body sections, while changing the lengths of the wires at the fixed handle, as shown in FIGS. 3A-3D. The configuration of the sheaths 24', 25' 26' and enclosed wires 24, 25, 26 does not affect the locomotion of the device 10 as long as there is slack between the handle 15 and the proximal body 14, some of which will be taken up with each forward step. In the figure, the heavy black line indicates which suction pad is active. Note that the configuration of the sheaths and enclosed wires between the handle 15 and proximal body 14 changes with each forward step, but the lengths remain constant.

Figure 3A:
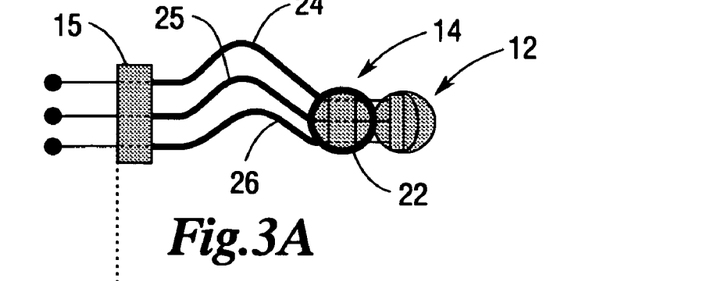
FIGS. 3A-3D illustrate forward locomotion of the robot.
Figure 3B:
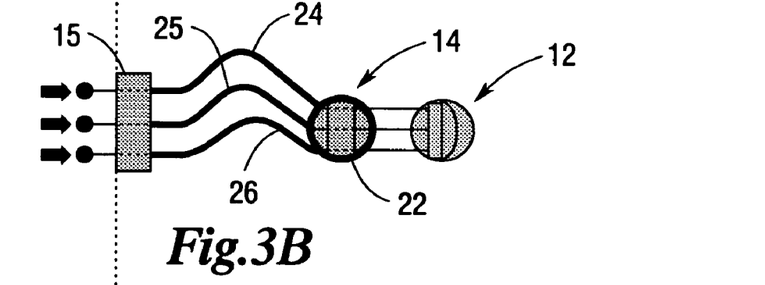
Figure 3C:
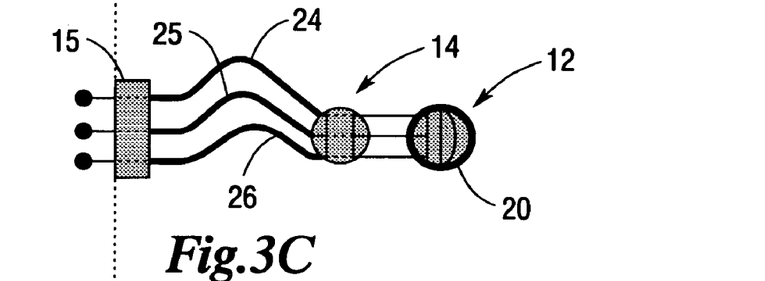
Figure 3D:
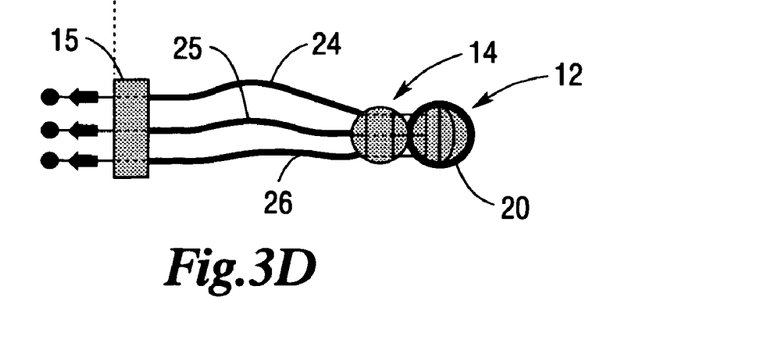
Figure 4A:
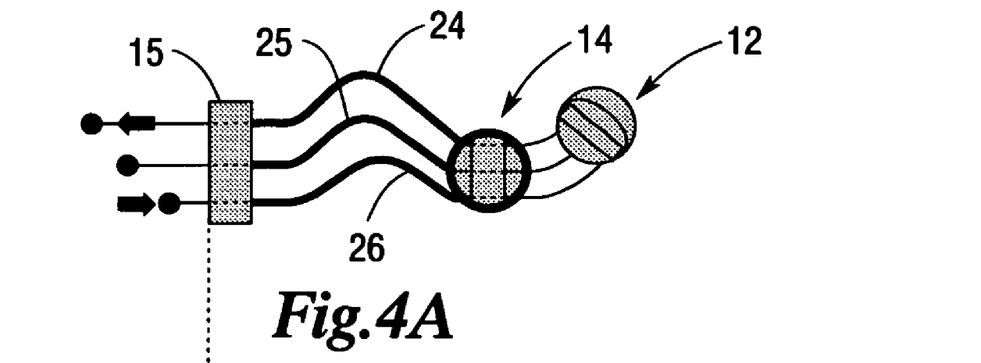
FIGS. 4A-4C illustrate side to side turns of the robot.
Figure 4B:
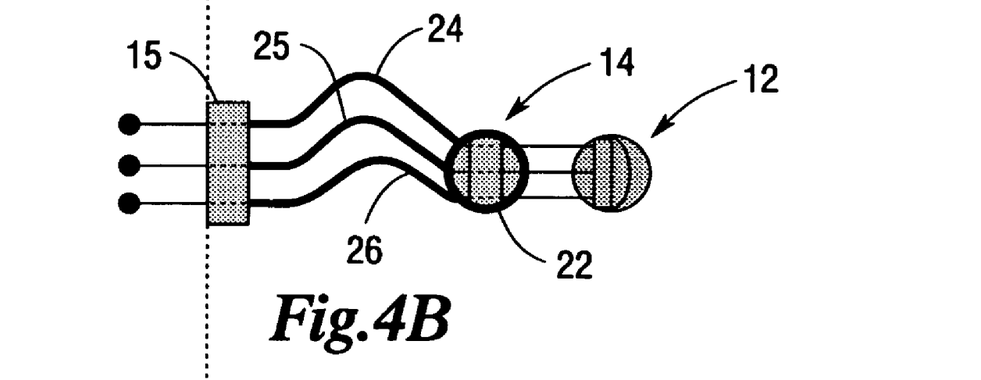
Figure 4C:
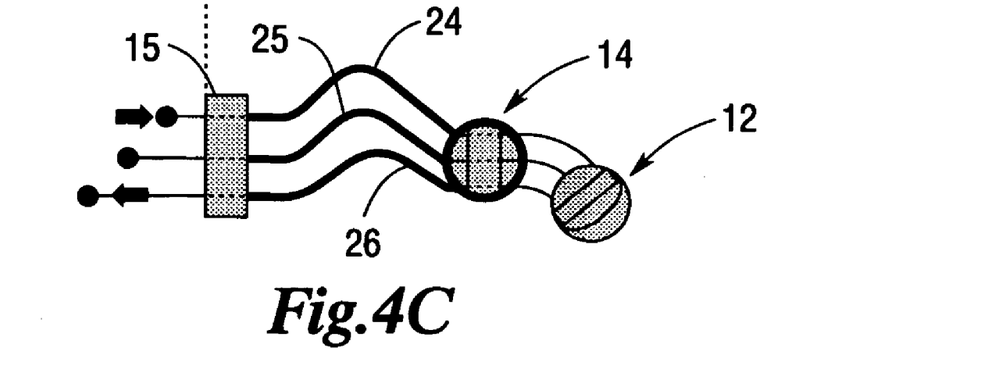

Between FIGS. 3A and 3B, while the proximal suction pad 22 is turned on, the wires 24, 25, 26 are moved forward causing distal body 12 to move forward by the same amount. In FIG. 3C, the proximal suction pad 22 is turned off and the distal suction pad 20 is turned on. In FIG. 4D, the compression in the sheaths 24', 25', 26' is released, causing the proximal body 14 to "catch up" with the distal body 12. Another forward step can now be taken by repeating the process. Turning can be achieved by differentially changing the lengths of the side wires as shown in FIGS. 4A-4C. The actuation of the wires at the handle may be performed manually, along with the opening and closing of the valves to the suction lines.

Figure 5A:
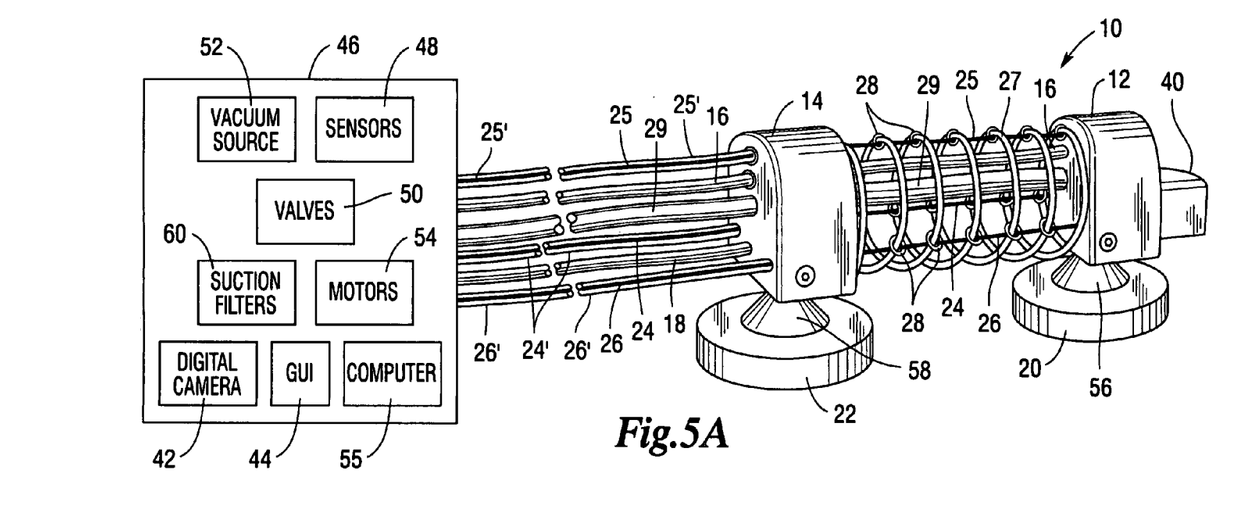
Figure 5B:
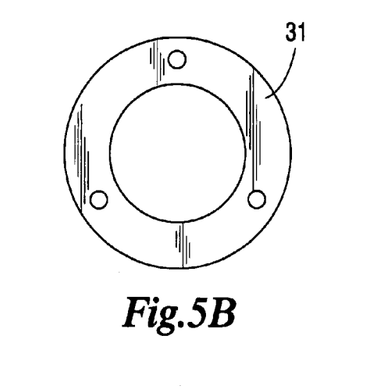
FIG. 5B illustrates a washer-like support spacer.

Another embodiment is illustrated in FIG. 5. In FIG. 5, components having similar functions and construction to those of FIGS. 1 and 2 have like reference numbers. The embodiment of FIG. 5 differs from the previous embodiment in several ways. For example, between the proximal body 14 and distal body 12 the wires 24, 25, 26 may be attached to a support spring 27 by eyelets 28 to prevent the wires 24, 25, 26 from bowing during turning and to ensure that the wires maintain an equal distance from one another. The support spring 27 may have a very low spring constant (e.g. k=0.012 N/mm) such that the restoring force is negligible as compared to that of the wires 24, 25, 26. As an alternative to the spring 27 and eyelets 28, a plurality of flat, washer-like structures 31 (See FIG. 5B) may be provided to maintain the proper spacing between wires 24, 25, 26. The plurality of washer-like structures 31 may be separated from one another by springs (not shown).

A 1.6 mm diameter commercial fiberscope 29, running longitudinally through the length of the device, may be fixed on the distal body 12 to provide visual feedback, with or without the use of an adjustable mirror 40. The images from the fiberscope 29 may be captured with a digital video camera 42 and displayed as a part of the graphical user interface (GUI) 44, both of which are part of a control system 46. The control system 46 may include sensors 48 for monitoring the vacuum supplied by suction lines 16, 18, electronically controlled valves 50 for determining which suction pad 20, 22 is operative, and vacuum source 52. The control system 46 may also include motors 54 for controlling movement of wires 24, 25 26. A computer 55 may be provided to control the various components in response to information input by the surgeon via the GUI 44 to control locomotion and other functions. Such a design allows for the motors 54, solenoid valves 50, etc. to be located outside the device 10. It is anticipated that the robot 10 may be either a disposable device or a reusable, sterilizable device.

In the embodiment of FIG. 5, the suction pads 20, 22 are connected to the bodies 12, 14 by means of flexible feet 56, 58, respectively. That enables the suction pads 20, 22 more freedom to conform to the surface of the organ. Meshes (not shown) may cover the bottom of the suction pads to keep out large particles, while suction filters 60 may be provided to remove fluids and small particles.

An aspect of the present invention is changing the frame of reference of the robot from that of the surgeon to that of the moving organ. The exact form and construction of the robot used to bring about that change of reference is not critical to this aspect of the invention. For example, although in the disclosed embodiments locomotion is achieved through the advancement of wires, either manually or through the activation of motors, others means of locomotion may be provided such as local (i.e. positioned on the robot) electric motors (operated with or without a tether), local ultrasonic motors (operated with or without a tether), as well as pneumatic actuators (typically operated with a tether). The means for prehension in the disclosed embodiment is suction. Alternative means of prehension may include synthetic gecko foot hair [Sitti M, Fearing R S (2003) Synthetic gecko foot-hair micro/nano-structures as dry adhesives. J Adhesion Sci Technol 17(8): 1055-1073] or a "tacky" foot. The actuation for treatment may include all the same alternatives as for locomotion. Finally, the device may operate with a tether having wires and pneumatic lines as disclosed above, with a tether having electric wires for local motors or video from a camera, or the device may operate without a tether. Tetherless models could be powered by a battery, the transcutaneous charging of a coil, etc., and could be controlled by local computing or through radio frequency transmissions. It will be understood by those of ordinary skill in the art that changing the frame of reference of the robot from that of the surgeon to that of the moving organ can be brought about by a wide variety of robots designed so as to be able to move within a loosely bounded body cavity. A loosely bounded body cavity refers to that space surrounding an organ such as, for example, the peritoneal space surrounding the liver, the pleural space surrounding the lungs, the pericardial space surrounding the heart, etc., in addition to the space within certain organs such as the heart or stomach.

Figure 6A:
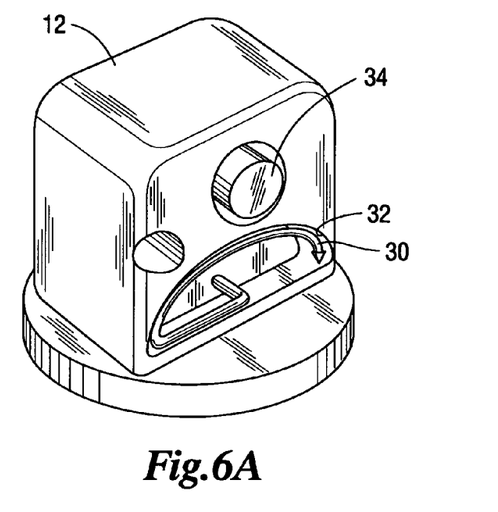

FIG. 6A illustrates an end effector (tool), which in this example is a needle 30 carried within a recess 32 in distal body 12. Distal body 12 also carries a means for providing images such as a fiberscope or camera, with or without some combination of lenses, mirrors, fiberoptics, etc. The needle 30 may used to perform epicardial electrode lead placement for cardiac resynchronization therapy (CRT) via subxiphoid videopericardioscopic access. A robot 10 equipped with the needle 30 can perform a minimally invasive suturing technique that can be used with a variety of epicardial pacing leads, both permanent and temporary.

Needle 30 is a high-strength needle for suturing that has a drive shaft (not shown) that runs along the long axis of the device 10, entered laterally and located below the midline of distal body 12. At the distal (working) end of this drive shaft is the needle 30 which is a segment (roughly 5 mm) that is bent 90° with respect to the drive shaft, forming the radius of a circle. The needle 30 will then terminate in a semicircular suturing portion. The lower half of the front end of the distal body 12 has a semicircular channel 32 into which the needle 30 recedes when it is not in use, protecting both the cardiac tissue and the needle 30.

Figure 6B:
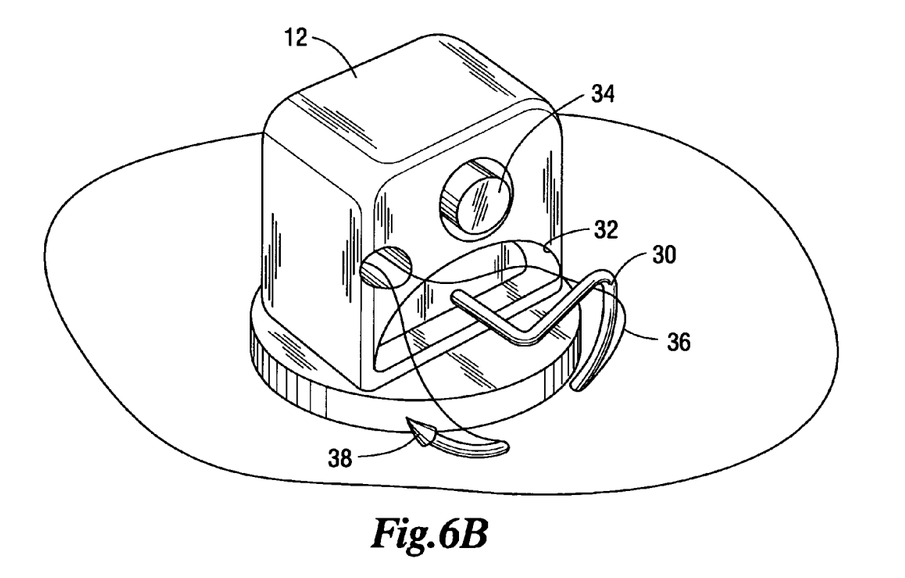
FIG. 6B illustrates the needle in operation.

The proximal end of the suture thread 36 remains outside the body. The distal end of the thread 36 is connected to a sharpened cap 38, which will fit snugly over the end of the needle 30. When the surgeon has positioned the distal body 12 at a desired work site, suturing will be performed by advancing the needle 30 from its recessed storage channel 32 (see FIG. 5B) and then rotating the drive shaft, forcing the semicircular needle 30 and the sharpened cap 38 with its suture thread 36 to pass through the tissue in an arc and exit again with the suture cap 38 still on the tip of the needle 30. A minimally invasive forceps (not shown), passing through an off-center working port of the robot 10 will be used to grasp the thread 36, lift the thread 36 and its cap 38 from the tip of the needle 30, and retract the cap 38 and distal end of the thread 36 all the way back through the cannula to the outside of the body. Here, the surgeon will knot the suture with his own hands, tying a single throw (or half of a square knot) in the thread. Once the single throw has been tied, the surgeon will place a wire with a slightly forked tip against the knot, with the knot resting in the notch of the fork, and will use the wire to push the knot all the way back against the epicardium. He will then tie a second throw and use the wire to push it forward until it meets the first throw, completing the knot. Given an ample supply of sutures fitted with sharpened caps, this technique can be repeated as many times as necessary, by placing each sharpened cap on the tip of the needle using the same forceps that is used to retrieve it from the needle.

The robot 10 will have a separate electrode channel that will allow passage of the electrode and its wire lead from outside the body into the pericardium to be sutured to the heart. The needle 30, forceps, wire "fork", suture with sharpened cap, and all supporting instrumentation needed for the suturing technique may be designed for sterilizability. Actuation from outside the body is the most feasible option for the forceps, because the forceps must be fully retractable to bring the tip of the suture thread back to the hand of the surgeon. Actuation of the needle for suturing may be performed locally by motors inside the robot, or from outside the body using a wire running through the cannula. Visual feedback for suturing may be provided by the same device used during locomotion.

Figure 7A:
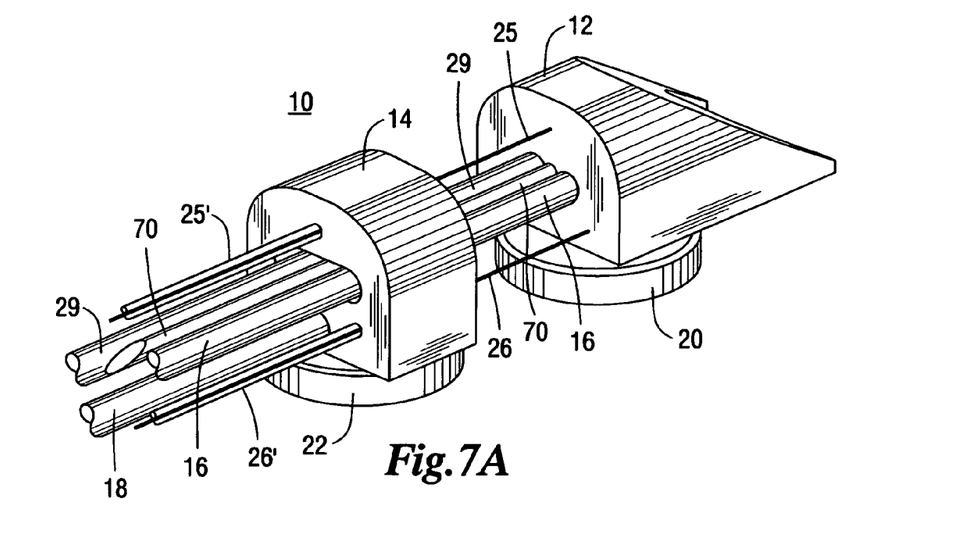
FIGS. 7A and 7B are an example of another type of end effector.
Figure 7B:
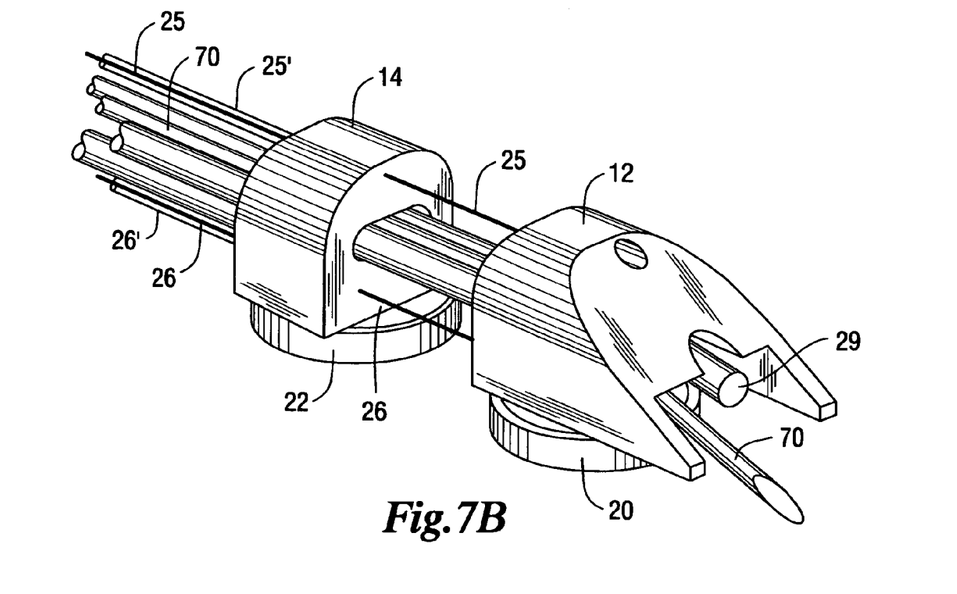

Another end effector (tool) is illustrated in FIGS. 7A and 7B. Like components carry the same reference numbers as used in the previous figures. In the device of FIGS. 7A and 7B, the washer-like structure 31 and spacer springs have been eliminated for purposes of clarity. The reader will understand that a plurality of washer-like structures 31 and spacer springs may be used in the embodiment of FIGS. 7A and 7B. An experiment using this end effector, needle 70, was performed on a pig. Through a 15 mm pericardial opening at the junction between the pericardium and the diaphragm at the midline, the device 10 was manually introduced inside the intact pericardium. Suction was applied to both suction pads. Stable contact with the epicardium of the beating anterior wall of the right ventricle was visually confirmed for a period of 30 seconds. The device 10 was then advanced across the left anterior descending coronary artery over the anterior wall of the beating left ventricle. Consistent stable contract with the epicardium of the beating left ventricle was observed. The device 10 was then further advanced over the left atrial appendage and stable fixation to the surface of the beating left atrium was confirmed.

Successful locomotion of the device 10 inside the intact pericardium was confirmed on the following areas: anterior wall of the beating right ventricle, anterolateral wall of the beating left ventricle, and anterior wall of the left atrial appendage. No gross epicardial or pericardial damage was observed. Because the present prototype has no outer shell between the bodies 12, 14, nothing prevented the pericardium from hanging down one or two millimeters between the bodies, and the leading edge of the proximal body 12, which was not tapered, then tended to snag somewhat on the pericardium. The pericardial sac also showed a tendency to adhere to all surfaces of the device 10 that it contacted, no matter how smooth. This seemed to be largely caused by drying of the sac due to exposure to air. Occasional infusions of normal saline solution were used for lubrication, which succeeded in alleviating the problem.

Two myocardial injections of tissue-marking dye were performed during the experiment. In each case, the device 10 walked to the desired site, locked down both bodies using suction, and then the surgeon performed the injection manually by advancing the 27 G custom needle 70 through a working port. For the first injection, the device 10 was positioned over the bifurcation of the left anterior descending coronary artery and the takeoff of the diagonal branch; the needle 70 was advanced into the left ventricular myocardium for 2-3 mm and 0.5 cc of dye was injected. The maximum force applied during injection was 0.72 N. The device 10 was then moved over the diagonal coronary artery and another injection of 0.5 cc of dye was made over the anterolateral wall of the left ventricle. The maximum force applied to the needle during the second injection was 1.15 N. No bleeding was observed after the needle 70 was withdrawn. Confirmation of successful injection was made at postoperative examination.

Because the device is tethered, pulling the tether provided a feasible method in the preliminary experiments to apply a tangential force to dislodge the device, without requiring the development of additional hardware that could be inserted somehow into the pericardial sac for testing. The force necessary to dislodge the device from the epicardium by pulling on the tether was measured with a force gauge while the device held onto the heart. A small clamp was applied to the part of the tether consisting of the three drive wires and their sheaths, and this clamp was attached to a handheld digital force gauge. The surgeon then pulled on the force gauge until the device was dislodged, and the gauge recorded the maximum force encountered during each trial. This test was performed three times with suction applied only to the distal body, three times with suction applied only to the proximal body, and three times with suction applied to both bodies. The results are presented in Table 1. No damage to the device resulted from these tests.

TABLE 1

| Body with suction applied | Number of trials | Mean (N) | Standard deviation (N) |
|---|---|---|---|
| distal | 3 | 1.62 | 0.37 |
| proximal | 3 | 3.23 | 0.70 |
| both | 3 | 4.48 | 0.43 |

During this experiment we demonstrated a technique for reattachment that can be used if the device is accidentally detached from the epicardium. This test was performed while the device was inside the intact pericardium. In this test, all suction was turned off, and, by manually twisting the tether, the device was intentionally rotated and was left lying on its right side on the epicardium. The suction in both pads 20, 22 was then turned on. By manually twisting the tether with a counterclockwise motion, the device was righted so that once again it correctly grasped the epicardial surface using the suction, and remained attached as before. The first time this test was performed, a video device was used to view the device 10, and by its presence lifted the pericardium somewhat, so that it did not lie as low on and around the device 10 as it normally would. Therefore, to avoid this effect, the video device was removed from the pericardium, and the test was repeated, this time with only the external video recorder monitoring the trial. Righting and reattaching of the device was performed successfully in both trials with no tissue damage and no damage to the device.

The ease with which the device can be retrieved from the pericardium was tested by measuring the maximum force encountered during extraction. The device was positioned normally inside the pericardium, standing upright on its feet with the distal body of the device near the left atrium, roughly 10 cm from the entry incision. All suction was turned off. The device was then retracted completely from the pericardium by pulling on the tether. This test was repeated three times, and the peak force measured during retrieval was recorded during each trial. The mean peak force measured was 2.49±0.51 N.

Figure 8:
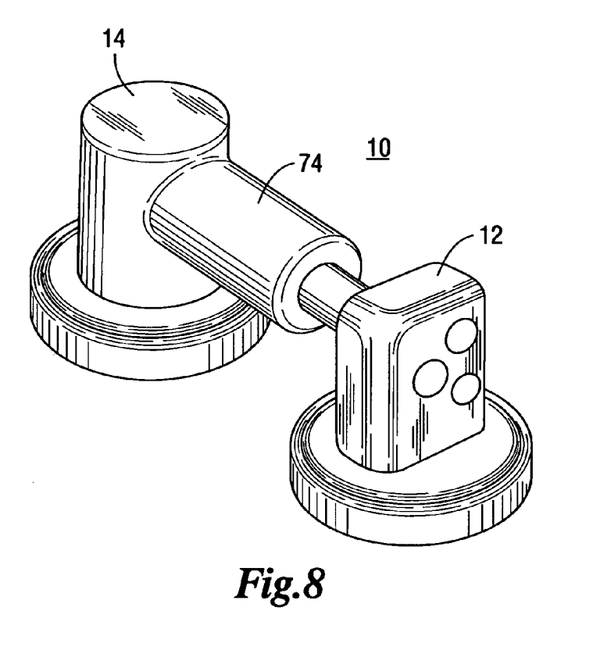
FIG. 8 illustrates a self contained embodiment of the device of the present disclosure.

FIG. 8 illustrates a self-contained design of the device 10, with the proximal body 14 shown at the upper left of the figure and the distal body 12 at the lower right. This design involves two motors for locomotion. One motor would be located in the vertical cylindrical body of the proximal body 14 and the other motor located in the horizontal cylinder 74 visible in the arm connecting the proximal 14 and distal 12 bodies. For clarity, a streamline housing, discussed below, is not shown in FIG. 8. The motors could receive power and instructions through a tether (not shown) or from an onboard battery and an onboard computer (not shown).

Figure 9A:
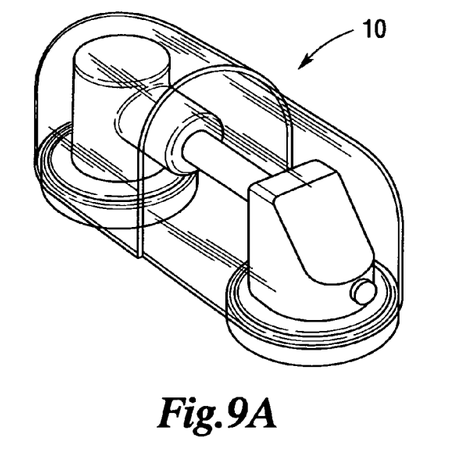
FIGS. 9A and 9B illustrate one example of a streamlined device of the present disclosure.
Figure 9B:
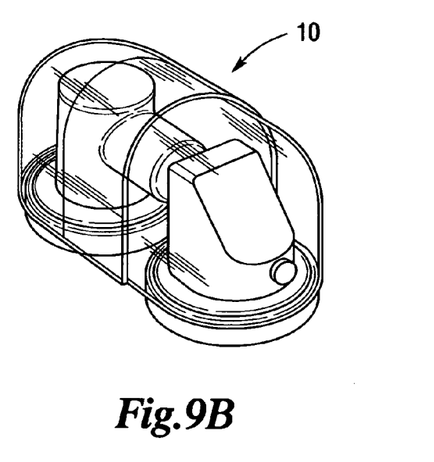

FIGS. 9A and 9B illustrate a device 10 with a capsular or pill-like design for streamline interaction with the pericardial sac. The device 10 has a two piece hard covering, one piece of which slides inside the other like a gelatin capsule of the sort often used for pills. FIG. 9A illustrates the device 10 in an extended phase of a step, i.e. maximum distance between the distal body 12 and proximal body 14, while FIG. 9B illustrates the contracted phase of the step, i.e. minimal distance between the proximal body 14 and distal body 12.

Figure 10A:
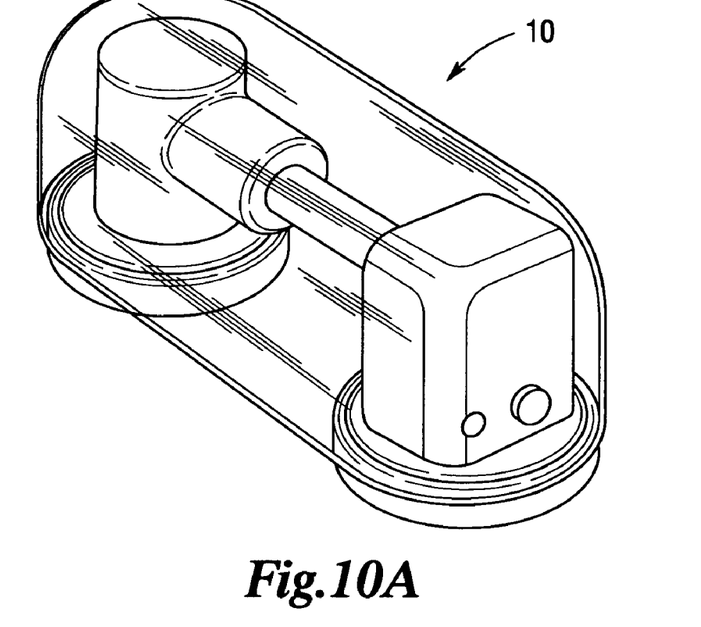
FIGS. 10A and 10B illustrate another example of a streamlined device of the present disclosure.
Figure 10B:
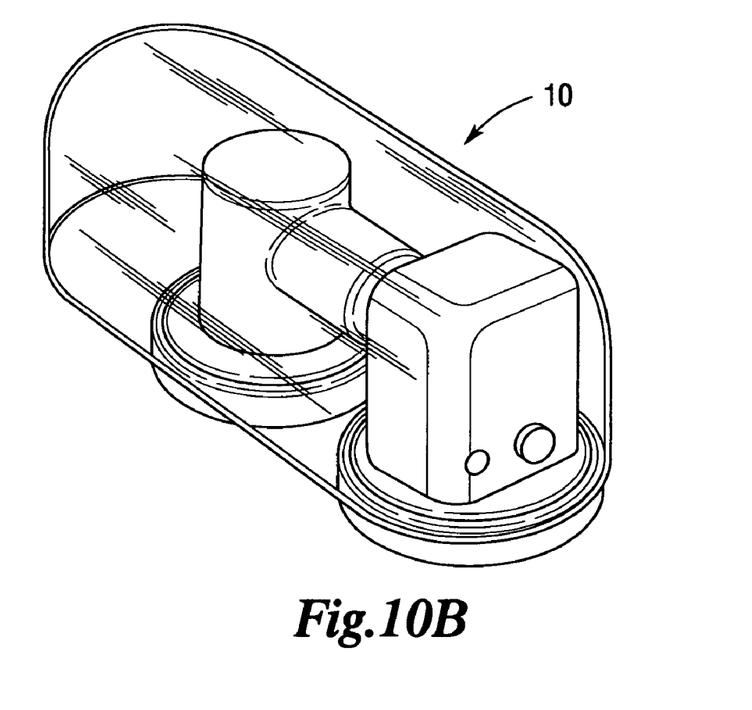

FIGS. 10A and 10B illustrate another design of the device 10 with a one-piece outer shell designed for streamline interaction with the pericardial sac. This design may be used in place of the design of FIGS. 9A and 9B should that design be found to cause pinching of the pericardium during locomotion. FIG. 10A illustrates the extended phase of a step while FIG. 10B illustrates the contracted phase of the step.

Figure 11A:
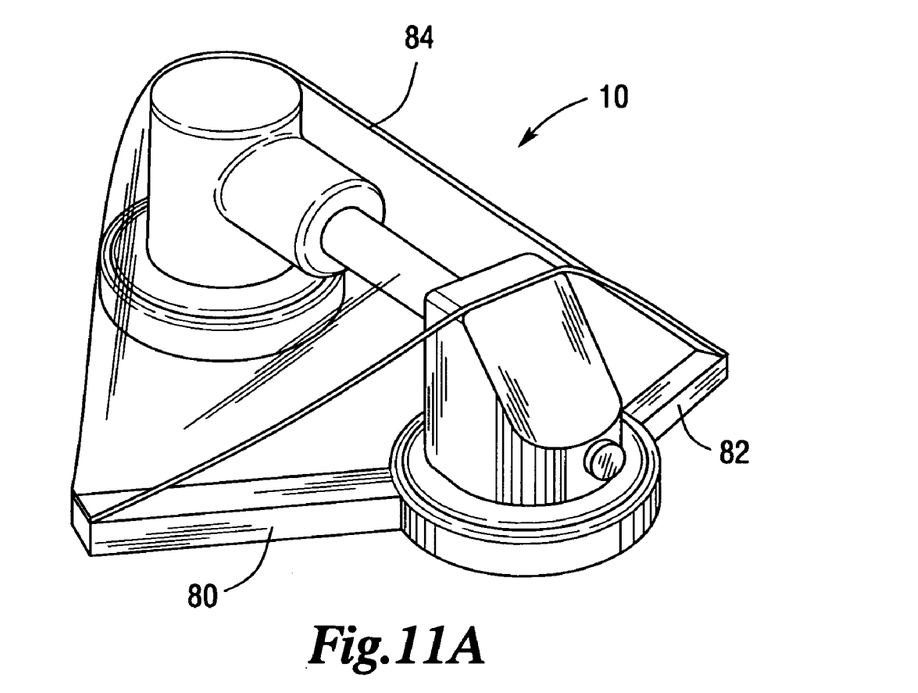
FIGS. 11A and 11B illustrate an embodiment of a device of the present disclosure having stabilization struts.
Figure 11B:
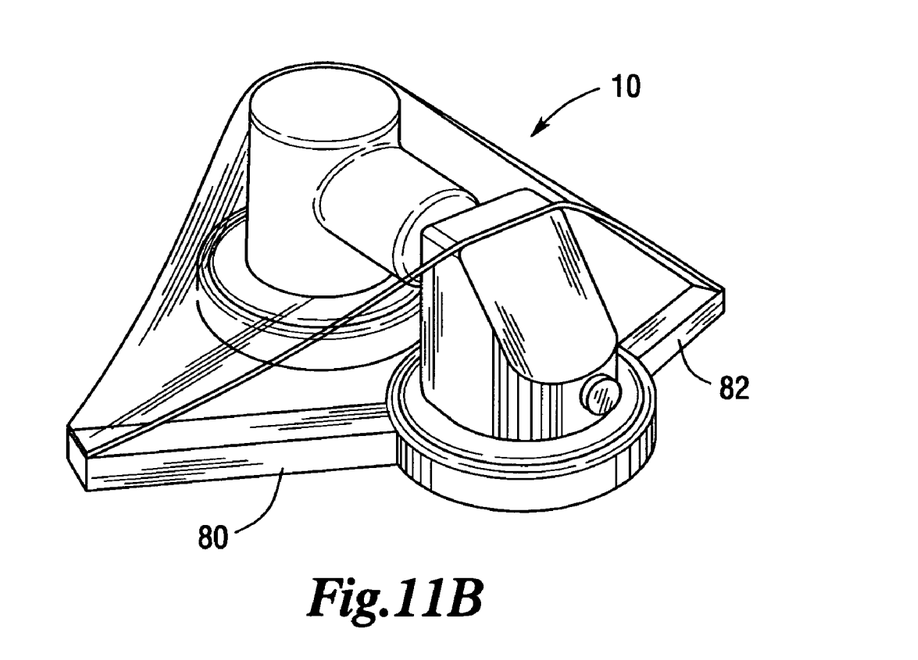

FIGS. 11A and 11B illustrate a design in which deployable outrigger-like struts 80, 82 are used if stronger safeguards against tipping become necessary. The outrigger-like struts 80, 82 would be foldable from the horizontal positions shown to vertical positions adjacent distal body 12 on both sides of the device 10. Once the device 10 is deployed within the pericardium, the struts 80, 82 may be moved from the horizontal to the vertical position shown in the figures to guard against tipping. If the struts 80, 82 evidence any tendency to snag the pericardium, a stretchable membrane 84 may be employed to cover both the device 10 and the struts 80, 82 as shown in the figures. FIG. 11A illustrates the extended phase of a step while FIG. 111B illustrates the contracted phase of the step.

Figure 12:
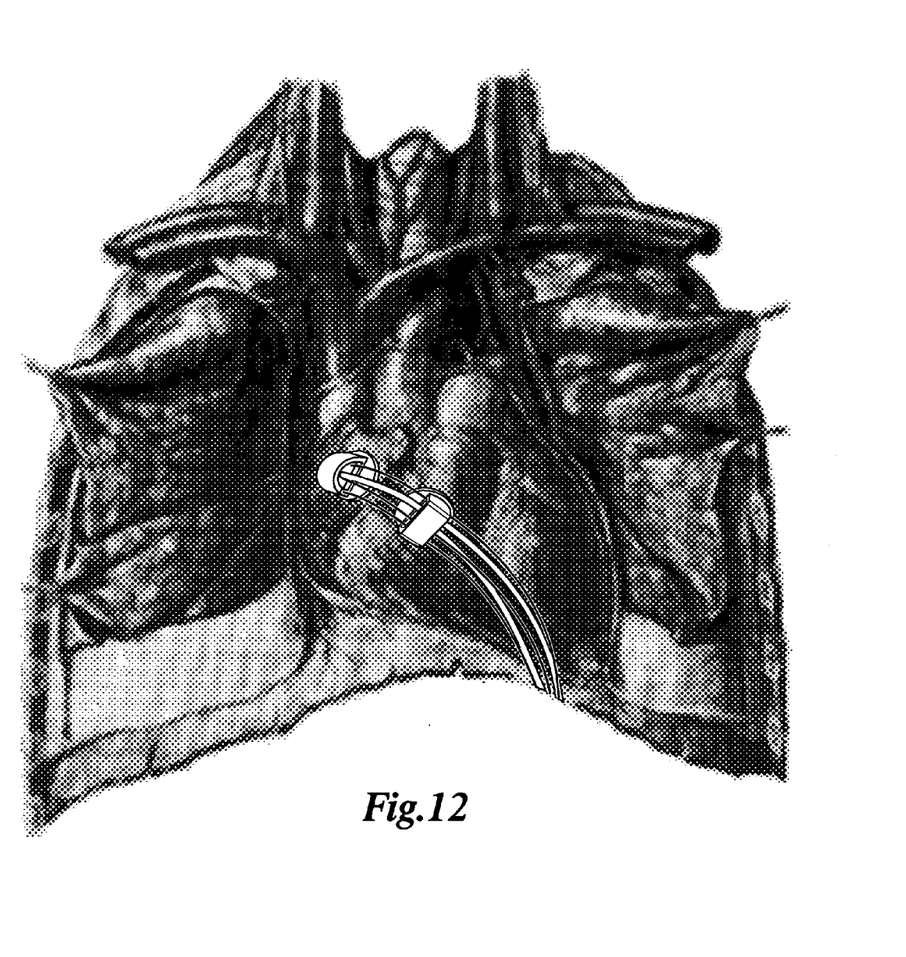
FIG. 12 is a conceptual illustration of the robot maneuvering on the surface of a heart to perform a procedure.

Turning to FIG. 12, in operation according to one aspect of the present invention, the device 10 will enter the pericardium and be placed on the epicardial surface of the heart using a rigid or flexible endoscope with a working port. The endoscope will be introduced into the pericardial sac through a port or limited incision beneath the xiphoid process of the sternum.

Once positioned appropriately with the endoscope under direct visual confirmation, the device 10 will grasp the epicardium using suction. The suction forces are applied through the two independent suction pads 20, 22 (see FIG. 5) that may be attached directly to bodies 12, 14 or through compliant or flexible feet 56, 58, respectively. The vacuum pressure is supplied to the suction pads 20, 22 by the vacuum source 52 through the operation of valves 50 and suction lines 16, 18 respectively. The vacuum source provides a vacuum pressure of $-0.08$ N/mm$^2$, which was found to be effective and safe for use in FDA approved cardiac stabilizers. The suction forces generated by this pressure have proven effective for our application, and did not damage the epicardial tissue. During locomotion, the vacuum pressure is monitored by the external pressure sensors 48 and regulated by computer-controlled solenoid valves 50, both located within the control system 46. Based on this pressure, the normal and tangential forces calculated to dislodge one of the bodies 12, 14 are 1.76 N and 0.87 N, respectively. Bench testing using a force gauge to dislodge the device from a poultry model verified normal and tangential forces of 2.01 N and 0.86 N. The tangential force that can be resisted by the device will be increased significantly by reducing the profile.

The device 10 will provide visual feedback to the surgeon during locomotion and administration of therapy. That can be accomplished using fiberoptics to relay the image from the distal end 12 of the device 10 to the camera 42 located in the control system 46. Alternatively, a CCD video camera can be mounted directly to the distal end 12 of the device 10. It may be possible to provide all of the necessary vision with a single visual sensor on a fixed mount. More likely, however, either the viewing head will be actuated for motion, or two imaging devices will be incorporated: one tangential to the surface of the organ (looking forward) for providing information for navigation, and the other normal to the surface (looking down) for providing a view of the area to receive attention. "Attention" is intended to be a broad term that includes all types of interventions in addition to all forms of testing, viewing or inspecting a site, etc., or any other activity that results in consideration being devoted to an organ or a portion of an organ.

The device 10 differs from prior art robotic surgical systems in several fundamental ways: (1) it operates within the reference frame of the heart rather than that of an operating table, (2) it will be introduced using a sub-xiphoid rather than an intercostal approach, obviating general endotracheal anesthesia (GETA), (3) it has locomotive capabilities, and (4) it will be relatively inexpensive and possibly disposable. For surgical procedures that can be performed completely within the pericardium, the device 10 will eliminate many of the limitations of these surgical systems.

Therapies administered from the device 10 will not require stabilization of the heart because the device 10 will be located in the same reference frame as the surface of the heart, rather than that of a fixed operating table. This eliminates the need for either endoscopic stabilizers, which require additional incisions, or cardiopulmonary bypass, which increases the complexity and risk of the procedure.

The teleoperative surgical systems in use today utilize laparoscopic manipulators and cameras and are introduced to the pericardial sac through several intercostal (between rib) incisions. These instruments must then pass through the pleural space before reaching the heart, which requires the collapsing of a lung. The delivery of the device 10 onto the heart will not require collapsing a lung because it will be introduced to the thoracic cavity through an incision made directly below the xiphoid process. The endoscope will then be pushed through the tissue and fascia beneath the sternum until the bare area of the pericardium is reached, never entering the pleural space. The scope will also be used to breach the pericardium, thus delivering the device 10 directly to the epicardium. Because the device 10 will not require the collapsing of a lung, it will also not require differential ventilation of the patient, and it is therefore possible that local or regional anesthesia could be used instead of general endotracheal anesthesia (GETA). As a result, a potential benefit is that the device 10 may enable certain cardiovascular interventions to be performed on an ambulatory outpatient basis, something that has never been done before.

The locomotive capabilities of the device 10 will enable it to reach virtually any position and orientation on the epicardium. This is not the case with rigid laparoscopes, which are limited to a relatively small workspace near the entry incision. In addition, these systems require the removal and re-insertion of the tools to change the operative field within a single procedure. The device 10, on the other hand, can easily change its workspace by simply moving to another region of the heart.

The da Vinci surgical system is very expensive and consists of a surgeon's computerized console and a patient-side cart with multiple large robotic arms. For procedures that can be performed within the pericardium, the device 10 will provide a small, extremely low-cost alternative to this system.

With proper development of end-effectors, the TEM will be able to perform epicardial cardiac procedures such as: cell transplantation, gene therapy, atrial ablation, and electrode placement for resynchronization myocardial revascularization. Devices such as an ultrasound transducer, diagnostic aid or other sensor, drug delivery system, therapeutic device, optical fiber, camera or surgical tool(s) may be carried by the device 10.

Procedures for organs other than the heart can be developed while remaining within the teachings of the present disclosure. Additionally, procedures on living bodies other than humans, e.g. pets, farm animals, race horses, etc. can be developed while remaining within the teachings of the present disclosure. Thus, while the present invention has been described in connection with preferred embodiments thereof, those of ordinary skill in the art will recognize that many modifications and variations are possible. The present invention is intended to be limited only by the following claims and not by the foregoing description which is intended to set forth the presently preferred embodiment.

What is claimed is:

1. A method of using a robot in a living body, the method comprising:
    inserting the robot into a pericardial space;
    attaching the robot to an epicardial surface of a pumping heart within the living body with at least one of a first suction device and a second suction device and actuating movement of the robot across a distance on the epicardial surface of the heart from a first position to a second position with a control system, the control system operable to actuate the first suction device and the second suction device in combination with control wires to translate and steer the robot in a selected direction from a plurality of selectable directions along the epicardial surface of the heart.

2. The method of claim 1 wherein said attaching step includes applying a suction with the first suction device while releasing the second suction device from the surface of the heart.

3. The method of claim 1 additionally comprising controlling the movement of the robot in any direction along the epicardial surface of the heart within the pericardial space with the control system.

4. The method of claim 3, comprising:
    establishing a length of cable between a control system and a proximal body of the robot and between the proximal body and a distal body, said cable passing through the proximal body and connected to the distal body, said cable carried in a flexible sheath between the control system and said proximal body;

anchoring the proximal body through the use of a prehension device;

moving the distal body forward by increasing the length of the cable between the proximal and distal body thereby causing said flexible sheath to deform;

anchoring the distal section through the use of a prehension device and releasing the proximal section; and moving the proximal body by allowing the flexible sheath to return to its undeformed state.

5. The method of claim 3 further comprising using the robot that includes a plurality of body sections that are interconnected such that the sections move relative to one another, said movement being responsive to said control system.

6. The method of claim 5 further comprising connecting the body sections using the control wires that include at least one of a plurality of manually actuated wires, cables or flexible drive shafts.

7. The method of claim 6 further comprising using the control system that includes a handle and said manually actuated wires, cables or flexible drive shafts which are carried, for at least part of their length, in sheaths.

8. The method of claim 1 comprising:
placing the robot on the surface of the heart;
affixing the robot to the surface so the robot is in the same frame of reference as the heart; and
enabling the robot to move along the surface while remaining at least partially attached to the surface and in the same frame of reference as the heart.

9. The method of claim 1 wherein said robot further comprises a shell covering.

10. The method of claim 1 further comprising using a tool attached to the robot.

11. The method of claim 10 wherein the tool comprises at least one of an ultrasound transducer, a diagnostic aid, a sensor, a drug delivery system, a therapeutic device, or a surgical tool.

12. The method of claim 10 further comprising using the tool for an electrode placement device.

13. The method of claim 1 further comprising using a sensor on the robot.

14. The method of claim 1 further comprising using the sensor to view a heart surface region.

15. The method of claim 14 further comprising using a camera or fiberscope with the robot.

16. The method of claim 14 further comprising using a fiberscope attached to the robot.

17. The method of claim 14 further comprising using a camera attached to the robot that generates an image of the heart.

18. The method of claim 1 further comprising using a placement device for subxiphoid transpericardial insertion of the robot.

19. The method of claim 18 further comprising using an endoscope for the placement device.

20. The method of claim 1 further comprising steering the robot having two orthogonal degrees of freedom to select a direction of movement.

21. A method for moving a device along a surface of a beating heart comprising:
endoscopically inserting a device into a living body;
attaching the device to an epicardial surface of a beating heart within the living body with at least one of a plurality of suction devices;
actuating movement of the device across the surface of the beating heart from a first position to a second position with a control system, the control system operable to actuate the suction devices in combination with control wires to steer the device in one of a plurality of selectable directions along the epicardial surface.

22. The method of claim 21 further comprising actuating movement of the device along the surface of the beating heart with the control system from outside of the living body.

23. The method of claim 21 further comprising using a plurality of cables that translate relative to at least a portion of the device to move the device across the surface.

24. The method of claim 21 further comprising using a tool on the device for placement of an electrode.

25. The method of claim 21 wherein the inserting step comprises inserting the device with a subxiphoid transpericardial placement.

26. The method of claim 21 further comprising using a camera to image the heart.

27. The method of claim 21 wherein the device comprises a first body section that attaches to the heart surface on a side of the device and a second body section that attaches to the heart surface on the same side of the device.

28. The method of claim 21 further comprising inserting the robot within a 20 mm diameter port.

* * * * *

UNITED STATES PATENT AND TRADEMARK OFFICE
CERTIFICATE OF CORRECTION

PATENT NO. : 8,162,925 B2  Page 1 of 1
APPLICATION NO. : 10/982670
DATED : April 24, 2012
INVENTOR(S) : Cameron N. Riviere et al.

It is certified that error appears in the above-identified patent and that said Letters Patent is hereby corrected as shown below:

In the Specification

Column 1, line 61, "Çavuğoğlu" should read --Çavuşoğlu--; and

Column 8, line 53, "FIG. 111B" should read --FIG. 11B--.

Signed and Sealed this
Eighteenth Day of March, 2014

Michelle K. Lee
*Deputy Director of the United States Patent and Trademark Office*